(12) United States Patent
Fujishiro et al.

(10) Patent No.: US 7,794,081 B2
(45) Date of Patent: Sep. 14, 2010

(54) SCANNING LASER OPHTHALMOSCOPE

(75) Inventors: Akihiro Fujishiro, Toyohashi (JP); Junichi Akita, Nukata-gun (JP)

(73) Assignee: Nidek Co., Ltd., Gamagori-shi (JP)

( * ) Notice: Subject to any disclaimer, the term of this patent is extended or adjusted under 35 U.S.C. 154(b) by 398 days.

(21) Appl. No.: 12/076,086

(22) Filed: Mar. 13, 2008

(65) Prior Publication Data

US 2008/0225226 A1 Sep. 18, 2008

(30) Foreign Application Priority Data

Mar. 16, 2007 (JP) .............................. 2007-068752

(51) Int. Cl.
*A61B 3/10* (2006.01)
(52) U.S. Cl. ....................................... 351/205; 351/221
(58) Field of Classification Search ......... 351/205–207, 351/221, 210, 213–217; 354/62
See application file for complete search history.

(56) References Cited

U.S. PATENT DOCUMENTS

| | | | |
|---|---|---|---|
| 4,765,730 A | 8/1988 | Webb | |
| 6,079,830 A * | 6/2000 | Kohayakawa | 351/211 |
| 7,198,367 B2 | 4/2007 | Akita et al. | |
| 2005/0231685 A1 | 10/2005 | Akita et al. | |
| 2009/0185136 A1* | 7/2009 | Isogai et al. | 351/221 |

FOREIGN PATENT DOCUMENTS

| | | |
|---|---|---|
| JP | A 05-199998 | 8/1993 |
| JP | A 2005-279121 | 10/2005 |
| JP | A 2006-239196 | 9/2006 |

* cited by examiner

*Primary Examiner*—Ricky L Mack
*Assistant Examiner*—Dawayne A Pinkney
(74) *Attorney, Agent, or Firm*—Oliff & Berridge, PLC

(57) ABSTRACT

A scanning laser ophthalmoscope comprises: a laser source that emits a laser beam; an irradiation optical system that scans the laser beam over a fundus two-dimensionally; a photoreceptor optical system that receives reflection from the fundus by using a photoreceptor element; an image processor that obtains an image of the fundus based on an output signal from the photoreceptor element; a monitor; and a controller that causes the monitor to display the obtained fundus image, wherein the image processor comprises a subtractive processing circuit that performs time-subtractive processing on the output signal from the photoreceptor element in a state where the output signal is input as an analog signal, and forms the fundus image based on the signal subjected to the subtractive processing.

5 Claims, 5 Drawing Sheets

FIG. 4
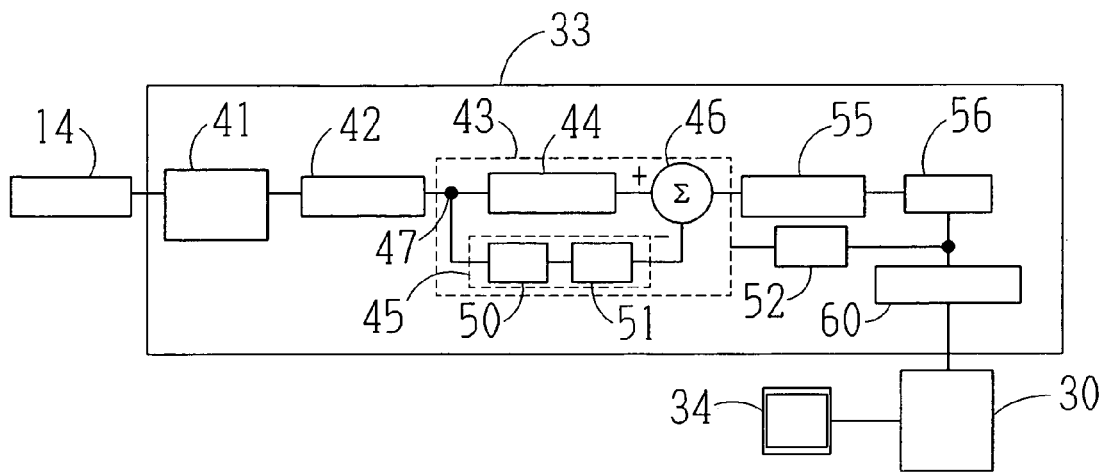
FIG. 5
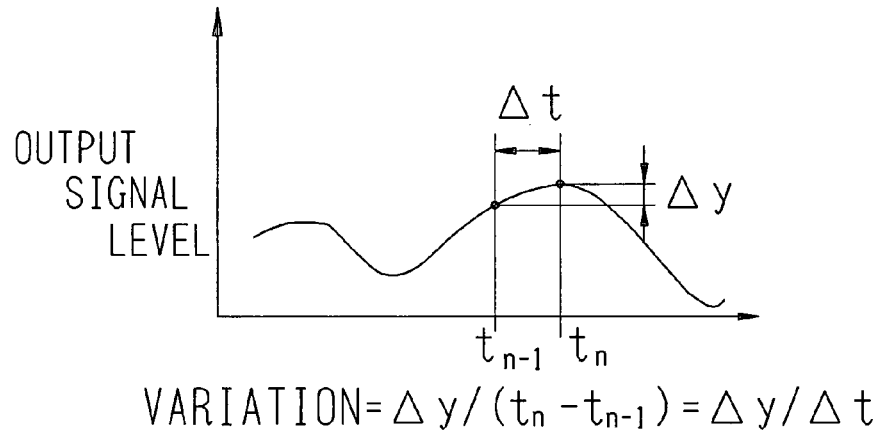
VARIATION= $\Delta y / (t_n - t_{n-1}) = \Delta y / \Delta t$
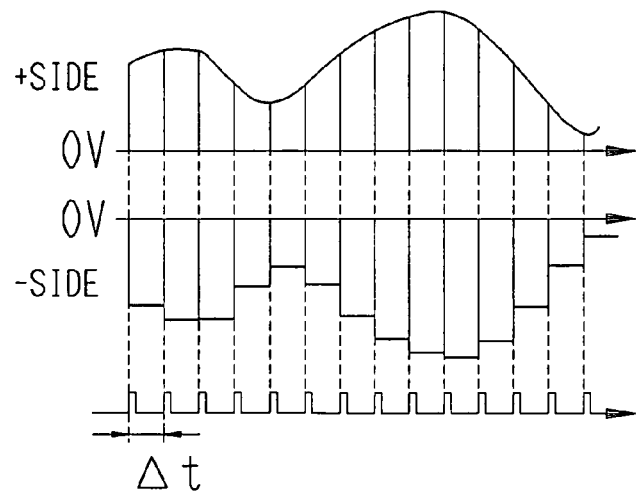
FIG. 6A
FIG. 6B
FIG. 6C

SCANNING LASER OPHTHALMOSCOPE

BACKGROUND OF THE INVENTION

1. Field of the Invention

The present invention relates to a scanning laser ophthalmoscope that obtains an image of the fundus of an examinee by scanning the fundus with a laser beam.

2. Description of the Related Art

A scanning laser ophthalmoscope is known that scans a laser beam two-dimensionally over the fundus of an examinee and receives reflection from the fundus, thereby obtaining an image of the fundus. According to such an apparatus, it is possible to irradiate a laser beam having predetermined wavelength characteristics as an excitation light onto the fundus of an examinee subjected to intravenous injection of a fluorescent agent and receive reflection from the fundus, thereby carrying out fluorescent fundus angiography (hereinafter abbreviated as FAG), indocyanine green fundus angiography (hereinafter abbreviated as ICG), etc.

However, according to fluorescent fundus photography (angiography), an image of the fundus is created in its fluorescent state and so liable to be fainted (blurred). For example, if a fluorescent agent partially leaks out of the blood vessels of the fundus in FAG, the part looks (is displayed) blurred whitely, thus making it difficult to identify an affected area. On the other hand, in ICG, the capillary vessels which are present in plenty under the retina pigment epithelium are in a strong fluorescent state, so that the image looks (is displayed) blurred whitely, thus making it difficult to identify an affected area.

SUMMARY OF THE INVENTION

It is an object of the present invention to provide a scanning laser ophthalmoscope that can obtain a fundus image effective in diagnosis and, more particularly to, a scanning laser ophthalmoscope that can make a fundus site clear which is observed by a monitor in fluorescent fundus photography (angiography).

To solve the above problems, the present invention features the following configuration.

(1) A scanning laser ophthalmoscope comprising:
a laser source that emits a laser beam;
an irradiation optical system that scans the laser beam over a fundus two-dimensionally;
a photoreceptor optical system that receives reflection from the fundus by using a photoreceptor element;
an image processor that obtains an image of the fundus based on an output signal from the photoreceptor element;
a monitor; and
a controller that causes the monitor to display the obtained fundus image,
wherein the image processor comprises a subtractive processing circuit that performs time-subtractive processing on the output signal from the photoreceptor element in a state where the output signal is input as an analog signal, and forms the fundus image based on the signal subjected to the subtractive processing.

(2) The scanning laser ophthalmoscope according to (1), wherein the subtractive processing circuit comprises a delay processing circuit that converts the analog-state output signal from the photoreceptor element into a digital signal and performs delay processing on it, and performs addition processing or subtraction processing on the signal subjected to the delay processing and the signal not subjected to the delay processing by respectively using an adder or a subtractor for the time-subtractive processing.

(3) The scanning laser ophthalmoscope according to (2), wherein the image processor synchronizes a pixel frequency employed when obtaining the signal subjected to the subtractive processing which is worthy of one pixel of the fundus image based on the signal subjected to the subtractive processing with a clock signal frequency employed when converting the analog-state output signal from the photoreceptor element into the digital signal by using the subtractive processing circuit.

(4) The scanning laser ophthalmoscope according to (1) wherein the image processor selectively forms the fundus image based on the signal subjected to the subtractive processing and the fundus image based on the signal not subjected to the subjective processing.

(5) The scanning laser ophthalmoscope according to (4), wherein:
the photoreceptor optical system comprises a filter that transmits a fluorescence generated at the fundus when it is irradiated with the laser beam and that can be inserted into and removed from an optical path of the photoreceptor optical system; and
the image processor forms the fundus image based on the signal subjected to the subtractive processing if the filter is inserted into the optical path and forms the fundus image based on the signal not subjected to the subtractive processing if the filter is removed from the optical path.

BRIEF DESCRIPTION OF THE DRAWINGS

FIG. 4 shows an outlined block diagram of an image processor;

FIG. 5 shows time-dependent changes of an output signal from a photoreceptor element;

FIGS. 6A-6C show processing by a delay processing circuit;

DESCRIPTION OF THE PREFERRED EMBODIMENTS

Figure 1:
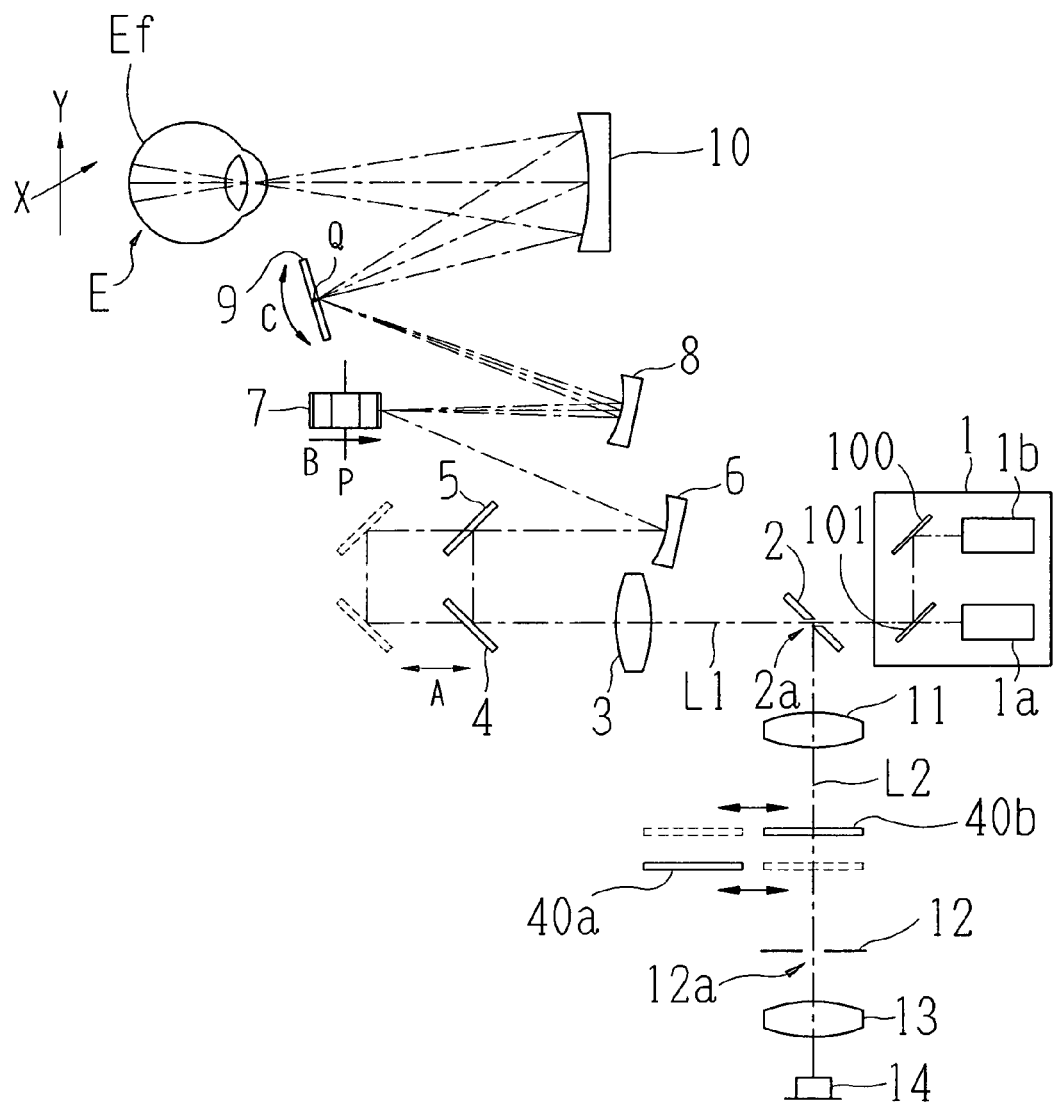
FIG. 1 shows an outlined configuration diagram of an optical system of a scanning laser ophthalmoscope in accordance with an embodiment of the present invention.

The following will describe an embodiment of the present invention with reference to the drawings. FIG. 1 shows an outlined configuration diagram of an optical system of a scanning laser ophthalmoscope in accordance with an embodiment of the present invention.

A beam emitting portion (beam emitter) 1 includes a first laser source 1a that emits a first laser beam having an infrared band wavelength, a second laser-source 1b that emits a laser beam having a visible band wavelength, a total reflection planar mirror 100, and a dichroic mirror 101 that transmits infrared light and reflects visible light. It is to be noted that in the present embodiment, the first laser source 1a emits a first laser beam having a wavelength in the vicinity of 790 nm and the second laser source 1b emits a second laser beam having a wavelength in the vicinity of 490 nm. The first beam emitted from the first laser source 1a passes through the dichroic mirror 101 and travels along an optical axis L1. The second beam emitted from the second laser source 1b is reflected by the mirror 100 and the dichroic mirror 101 so that it may be coaxial with the first beam and travel along the optical axis L1.

The first beam and the second beam from the beam emitting portion 1 pass through a central opening 2a (through whose approximate center the optical axis L1 passes) in an apertured mirror 2 and a lens 3 and are reflected by total reflection planar mirrors 4 and 5 as well as a total reflection concave mirror 6 and then made incident upon a polygon mirror 7. The first and second beams reflected by the polygon mirror 7 are reflected by a total reflection concave mirror 8 and made incident upon a galvano mirror 9. The first and second beams reflected by the galvano mirror 9 are reflected by a total reflection concave mirror 10 and collected to the fundus Ef of an examinee's eye E. Those optical components constitute an irradiation optical system that irradiates (applies) the first and second beams onto the fundus Ef.

It is to be noted that the mirrors 4 and 5 are arranged so as to be movable in the direction of arrow A for the purpose of focusing (diopter movement) through changing of an optical path length. The polygon mirror 7 is rotated around an axis P in the direction of arrow B in order to scan the first and second beams over the fundus Ef in the direction of arrow X. The galvano mirror 9 is oscillated (rotated) around an axis Q in the direction of arrow C in order to scan the first and second beams over the fundus Ef in the direction of arrow Y perpendicular to the arrow X direction. Those beam scanners will scan the first and second beams over the fundus Ef two-dimensionally.

The first and second beams scanned over the fundus Ef and reflected by it follow backward through the above-described irradiation optical system to be reflected by a peripheral face of the opening 2a in the apertured mirror 2 and travel along an optical axis L2. The opening 2a is roughly conjugate with the pupil of the eye E owing to the lens 3. The first and second beams reflected by the apertured mirror 2 pass through a lens 11 to be focused at a pinhole 12a (through whose approximate center the optical axis L2 passes) in a pinhole plate 12. The pinhole 12a is roughly conjugate with the fundus Ef owing to the lenses 3 and 11. The first and second beams focused at the pinhole 12a pass through a lens 13 to be received by a photoreceptor element 14 that has photographic sensitivity in the infrared band and the visible band. Those optical components constitute a photoreceptor (photographing) optical system.

It is to be noted that although in the present embodiment, the diameter of the pinhole 12a has been fixed, the diameter may be variable so that the contrast and the luminance of an image of the fundus Ef to be obtained can be changed. Further, although the present embodiment has employed an avalanche photodiode (APD) as the photoreceptor element 14, the present invention is not limited to it; for example, a known photoreceptor element can be used.

Figure 2A:
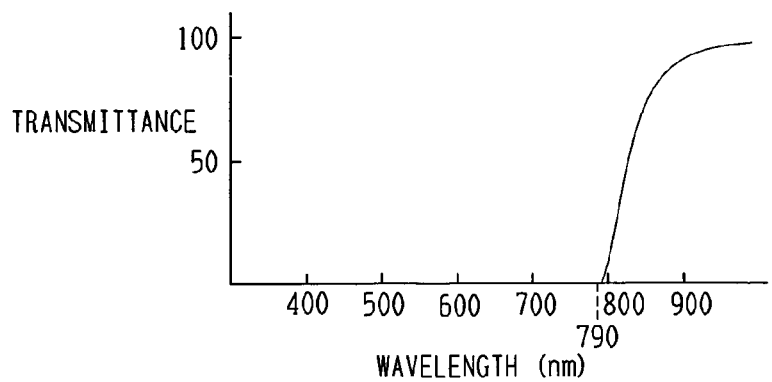
FIG. 2A shows one example of spectral transmission characteristics of a filter for use in indocyanine green fundus angiography.
Figure 2B:
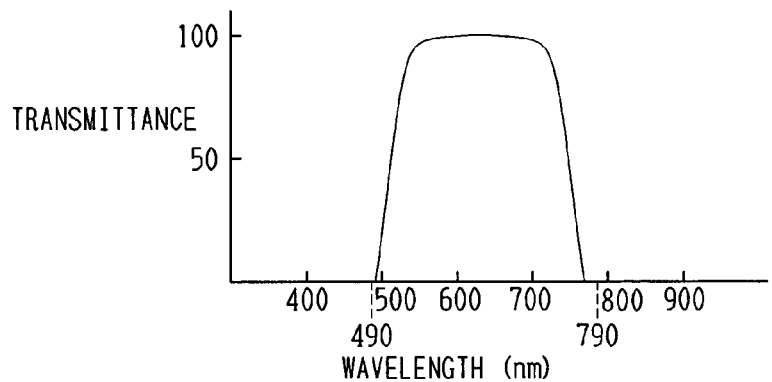
FIG. 2B shows one example of spectral transmission characteristics of a filter for use in fluorescent fundus angiography.

A first filter 40a for use in ICG and a second filter 40b for use in FAG can be inserted into and removed from the optical path of the photoreceptor optical system. It is to be noted that the first filter 40a and the second filter 40b may be disposed anywhere along the optical path (optical path ranging from the apertured mirror 2 to the photoreceptor element 14) of the photoreceptor optical system that does not overlap with the optical path of the irradiation optical system. The first filter 40a has spectral transmission characteristics such as shown in FIG. 2A and the second filter 40b has spectral transmission characteristics such as shown in FIG. 2B. The first filter 40a cuts off the first and second beams reflected by the fundus Ef and second fluorescence generated at the fundus Ef with the second beam as an excitation light owing to the irradiation with the second beam. Further, it transmits first fluorescence generated at the fundus Ef with the first beam as an excitation light owing to the irradiation with the first beam. On the other hand, the second filter 40b cuts off the first and second beams reflected by the fundus Ef and the first fluorescence from the fundus Ef. Further, it transmits the second fluorescence from the fundus Ef.

Figure 3:
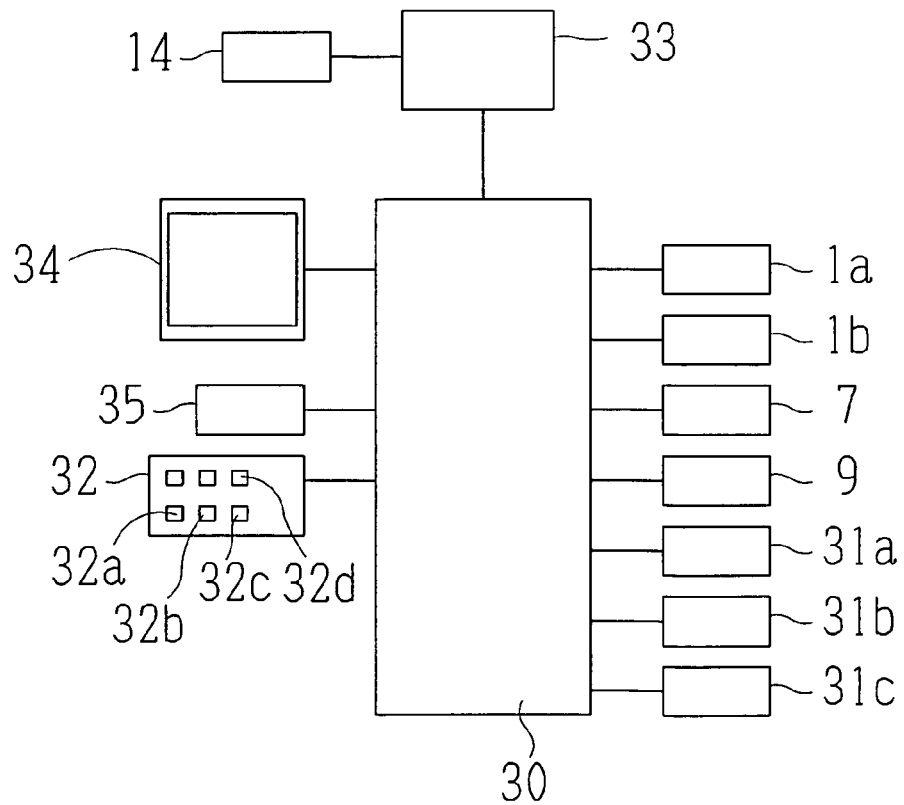
FIG. 3 shows an outlined block diagram of a control system of the present apparatus.

FIG. 3 is an outlined block diagram of a control system of the present apparatus.

To a controller (calculation control portion) 30 that controls the entirety of the apparatus are connected the laser source 1a, the laser source 1b, the polygon mirror 7, the galvano mirror 9, the photoreceptor element 14, a moving portion 31a for the mirrors 4 and 5, a moving portion 31b for the first filter 40a, a moving portion 31c for the second filter 40b, an operating portion 32, an image processor (image processing portion) 33 that obtains (forms) an image of the fundus Ef based on an output signal from the photoreceptor element 14, a monitor (display portion) 34, a memory (storage portion) 35, etc. The controller 30 causes the monitor 34 to display the fundus image obtained by the image processor 33. The operating portion 32 is equipped with an input portion that inputs refractive power of the eye E for the purpose of diopter movement and various apparatus operating switches such as a save switch that stores data of the fundus image displayed on the monitor 34 in the memory 35, a photographing switch 32a for ordinary fundus photographing, a photographing switch 32b for ICG, a photographing switch 32c for FAG, and a photographing switch 32d for displaying a differential fundus image (which will be detailed later).

FIG. 4 is an outlined block diagram of the image processor 33. The image processor 33 has a subtractive processing circuit 43 that performs time-subtractive processing on an analog-state output signal from the photoreceptor element 14. The output signal from the photoreceptor element 14 is input (applied) via a noise reduction circuit 41 and an amplification circuit 42 to the subtractive processing circuit 43, an output signal from which subtractive processing circuit 43 is input (applied) to an imaging circuit 60 via an amplification circuit 55 and an output circuit 56. Based on an output signal from the output circuit 56, the imaging circuit Go performs imaging processing.

The amplification circuits 42 and 55 amplify the voltage of the received analog signal as it is. The noise reduction circuit 41 reduces power supply noise and sensor noise contained in the output signal from the photoreceptor element 14 (for example, transmits the output signal by restricting AC coupling and a frequency band). The subtractive processing circuit 43 has a separating portion 47 that separates this circuit between a plus-side circuit and a minus-side circuit and an adder 46 that adds up separated signals through coupling in such an arrangement that a holding circuit 44 that holds and stabilizes the received signal is disposed as the plus-side circuit and a delay processing circuit 45 that temporally delays the received signal is disposed as the minus-side circuit. The separating portion 47 has a circuit switchover portion to switch between the case of inputting the output signal to both of the plus-side circuit and the minus-side circuit and the case of inputting it only to the plus-side circuit. It is to be noted that in the present embodiment, the delay processing circuit 45 is constituted of an analog/digital conversion circuit (hereinafter abbreviated as A/D conversion circuit) 50 and a digital/analog conversion circuit (hereinafter abbreviated as D/A conversion circuit) 51. Further, the A/D conversion circuit 50 and the D/A conversion circuit 51 operate synchronously with each other based on a clock signal from a clock signal generator 52. With this, a frequency from the clock signal generator 52 is used to delay by a predetermined lapse of time $\Delta t$ the analog signal (output signal) which is output from the photoreceptor element 14 and input to the minus-side circuit.

The following will describe the operations in the scanning laser ophthalmoscope having the above-described configuration. Specifically, a method for performing FAG will be described below.

When power is applied to the apparatus, as initial setting, the controller 30 causes the first laser source 1$a$ to emit the infrared first beam as an illumination light for the purpose of observation. The controller 30 further controls the separating portion 47 of the subtractive processing circuit 43 so that the output signal from the photoreceptor element 14 may be input only to the plus-side circuit (for imaging without performing the subtractive processing). That is, in the initial setting, the controller 30 creates an image based on the output signal from the photoreceptor element 14 by using the image processor 33 without performing the subtractive processing at the subtractive processing circuit 43 and displays on the monitor 34 a fundus image (so-called an ordinary fundus image) in which the magnitude of the output value of the output signal is expressed two-dimensionally.

If data of refractive power of the eye E measured by an eye refractive power measuring apparatus etc. beforehand is input using the operating portion 32, the controller 30 stores the input refractive power data into the memory 35 and drives the moving portion 31 to move the mirrors 4 and 5, thereby performing the diopter movement. Next, the apparatus is moved after the diopter movement, to irradiate the fundus Ef with the first beam for the purpose of such alignment that a desired fundus image may be displayed on the monitor 34. In this case, the controller 30 drives the polygon mirror 7 and galvano mirror 9 to thereby scan the first beam over the fundus Ef two-dimensionally.

The image processor 33 obtains the image of the fundus Ef based on the output signal from the photoreceptor element 14 of the first beam reflected by the fundus Ef in a scanning range due to the polygon mirror 7 and the galvano mirror 9 Based on the image signal output from the image processor 33, the controller 30 sequentially displays each horizontal line's worth of the image vertically downward from the top in the display region of the monitor 34 (as the reflecting surface of the polygon mirror 7 rotates, one horizontal line's worth of the fundus image is obtained, and as the galvano mirror 9 oscillates downward, one vertical line's worth of the fundus image is obtained). Through such sequential display control, the controller 30 causes the monitor 34 to display a photographing range of the fundus Ef in which the laser beam has been scanned two-dimensionally as one image (one frame's worth of the image) Further, if the image is displayed over the entirety of the display region of the monitor 34, the controller 30 turns the galvano mirror 9 back to its angle of reflection at the time of start of scanning and drives it to scan the laser beam downward over again.

The controller 30 creates, by using the image processor 33, the image based on the output signal from the photoreceptor element 14 without subtracting this signal, thereby displaying the ordinary fundus image on the monitor 34. When alignment is completed, the fluorescent agent for the purpose of FAG is intravenously-injected to the eye E, and if the photographing switch 32$c$ is pressed, the controller 30 drives the moving portion 31$c$ to insert the second filter 40$b$ into the optical path of the photoreceptor optical system. It then causes the second laser source 1$b$ to emit the second beam and stops the emission of the first beam from the first laser source 1$a$. As the fluorescent agent for FAG circulates through the eye E, the second fluorescence is excited (generated) by the second beam which the fundus Ef has been irradiated with and received by the photoreceptor element 14. Based on the output signal from the photoreceptor element 14, the image processor 33 obtains a fluorescent fundus image.

FAG is carried out on the basis of preset frame rate and resolution. It is to be noted that the frame rate and the resolution may be fixed or set with a setting switch, not shown, on the operating portion 32. The controller 30 rotates the polygon mirror 7 so that set values of the frame rate and the resolution may be obtained. Further, to obtain the set values of the frame rate and the resolution, it oscillates the galvano mirror 9 in such a manner as to match the rotating speed of this polygon mirror 7. As aforementioned, through the one-directional rotation of the polygon mirror 7 and the one-directional oscillation of the galvano mirror 9 (downward in the present embodiment), one frame's worth of the fluorescent fundus image to be displayed on the monitor 34 will be obtained.

It is to be noted that if the photographing switch 32$d$ is pressed in a condition where the fluorescent fundus image is displayed on the monitor 34, the controller 30 controls the separating portion 47 in the subtractive processing circuit 43 to input the output signal to each of the plus-side circuit and the minus-side circuit. That is, if the photographing switch 32$d$ (display mode selecting switch) is pressed, the controller 30 switches mode setting based on the resultant input signal so that the subtractive processing circuit 43 may perform the subtractive processing on the output signal from the photoreceptor element 14. In such a manner, an ordinary fundus image display mode is switched to a differential fundus image display mode in which the monitor 43 displays a differential fundus image which is formed on the basis of the signal subjected to the subtractive processing.

As shown in FIG. 4, the output signal from the photoreceptor element 14 undergoes noise reduction through the noise reduction circuit 41 and is amplified by the amplification circuit 42 and then separated between the plus-side circuit and the minus-side circuit by the separating portion 47 in the subtractive processing circuit 43. In this case, the polarity of the output signal separated to the minus-side circuit is reversed to the negative side by a reversing circuit disposed on the separating portion 47. It is to be noted that in the present embodiment, a plus-or-minus reference is defined on whether the voltage value of the output signal is greater than a predetermined reference voltage, so that a value larger than the reference voltage is determined as being plus and a value smaller than that is determined as being minus. For example, if the reference voltage is set to +3V, the output signal's voltage value of +4V is determined as being plus by 1V (+1V) and the output signal's voltage value of +2V is determined as being minus by 1V (−1V).

The output signal (plus signal) separated to the plus-side circuit is input to the adder 46 via the holding circuit 44. On the other hand, the output signal separated to the minus-side circuit is held by the delay processing circuit 45 for a predetermined lapse of time (for example, a minute lapse of time Δt) to provide a signal (minus signal) delayed by the predetermined lapse of time with respect to the plus signal, which is then input to the adder 46.

In such a manner, the adder 46 adds up the output signal (plus signal) separated to the plus-side circuit and the output signal (minus signal) separated to the minus-side circuit and delayed, thereby detecting a differential voltage between the plus signal and the minus signal (subtractive processing). In this case, as shown in FIG. 5, since the minus signal has delay time Δt (is delayed by time Δt) with respect to the plus signal, by adding up these, a time-dependent change Δy/Δt is obtained of the output signal from the photoreceptor element 14. Therefore, information (differential information) is obtained of a time-dependent gradient of the output signal from the photoreceptor element 14. Further, no quantizing circuit (for example, A/D conversion circuit) for quantization of the output signal is disposed between the photoreceptor element 14 and the subtractive processing circuit 43, so that the analog-state output signal from the photoreceptor element 14 will undergo as it is. It is to be noted that the same subtractive processing can be carried out even if the reversing circuit is not disposed to the minus-side circuit of the separating portion 47 and the adder 46 is replaced with a subtractor.

FIGS. 6A-6C are charts showing processing by the delay processing circuit 45. FIG. 6A shows a waveform chart of the output signal (plus signal) that is input to the plus-side circuit and not passed through the delay processing circuit 45, FIG. 6B shows a waveform chart of the output signal (minus signal) that is input to the minus-side circuit and delayed by time Δt through the delay processing circuit 45, and FIG. 5C shows a waveform chart of the clock signal from the clock signal generator 52 The analog signal input to the A/D conversion circuit 50 is converted into the digital signal based on the clock signal from the clock signal generator 52. Thus, the digital signal delayed by time Δt is created. Then, the digital signal is input to the D/A conversion circuit 51 to be converted into the analog signal and input to the adder 46. In this case, a resolution is raised beforehand both in A/D conversion and D/A conversion. The resolution in this case should preferably be not greater than a noise level.

The signal thus subjected to the subtractive processing is amplified by the amplification circuit 55 and input to the imaging circuit 60 via the output circuit 56. The imaging circuit 60 creates the fundus image based on the subtractive-processed signal, that is, the differential fundus image in which a time-dependent variation of the output signal is obtained. Then, the differential fundus image is output to the monitor 34 and/or the memory 35. In such a manner, the differential fundus image based on the time-dependent variation of the output signal from the photoreceptor element 14 will be displayed on the monitor 34 and stored in the memory 35. Further, differential fundus images continually obtained at a predetermined frame rate will be displayed on the monitor 34 consecutively, thereby being displayed as a moving image. Further, the differential fundus images are stored in the memory 35 consecutively, thereby being stored as the moving image.

It is to be noted that in the subtractive processing (differential processing) and the imaging by the image processor 33, it is preferable that a pixel frequency employed when obtaining the subtractive-processed signal which is worthy of one pixel of the differential fundus image based on the subtractive-processed signal may be synchronized with the clock signal frequency employed when converting the analog-state output signal into the digital signal by the A/D conversion circuit 50 in the subtractive processing circuit 43 by using the clock signal generator 52. Thus, an interval for each pixel of the differential fundus image to be imaged agrees with the interval of time Δt, thereby making the differential fundus image even and clear.

Since the output signal from the photoreceptor element 14 undergoes the subtractive processing prior to being quantized as described above, this output signal is input to the subtractive processing circuit 33 where it is subjected to the subtractive processing as the analog signal, so that its minute time-dependent changes are detected. Then, the differential fundus image is created on the basis of that signal subjected to the subtractive processing as the analog signal, thereby emphasizing its differences in reflectance of the laser beam. Therefore, if this differential fundus image is displayed on the monitor 34, it looks sharpened more than the ordinary fundus image not subjected to the subtractive processing and the minute irregularities in the surface of the fundus Ef are made clear, thereby making it easy to identify an affected area on the fundus Ef.

Figure 7:
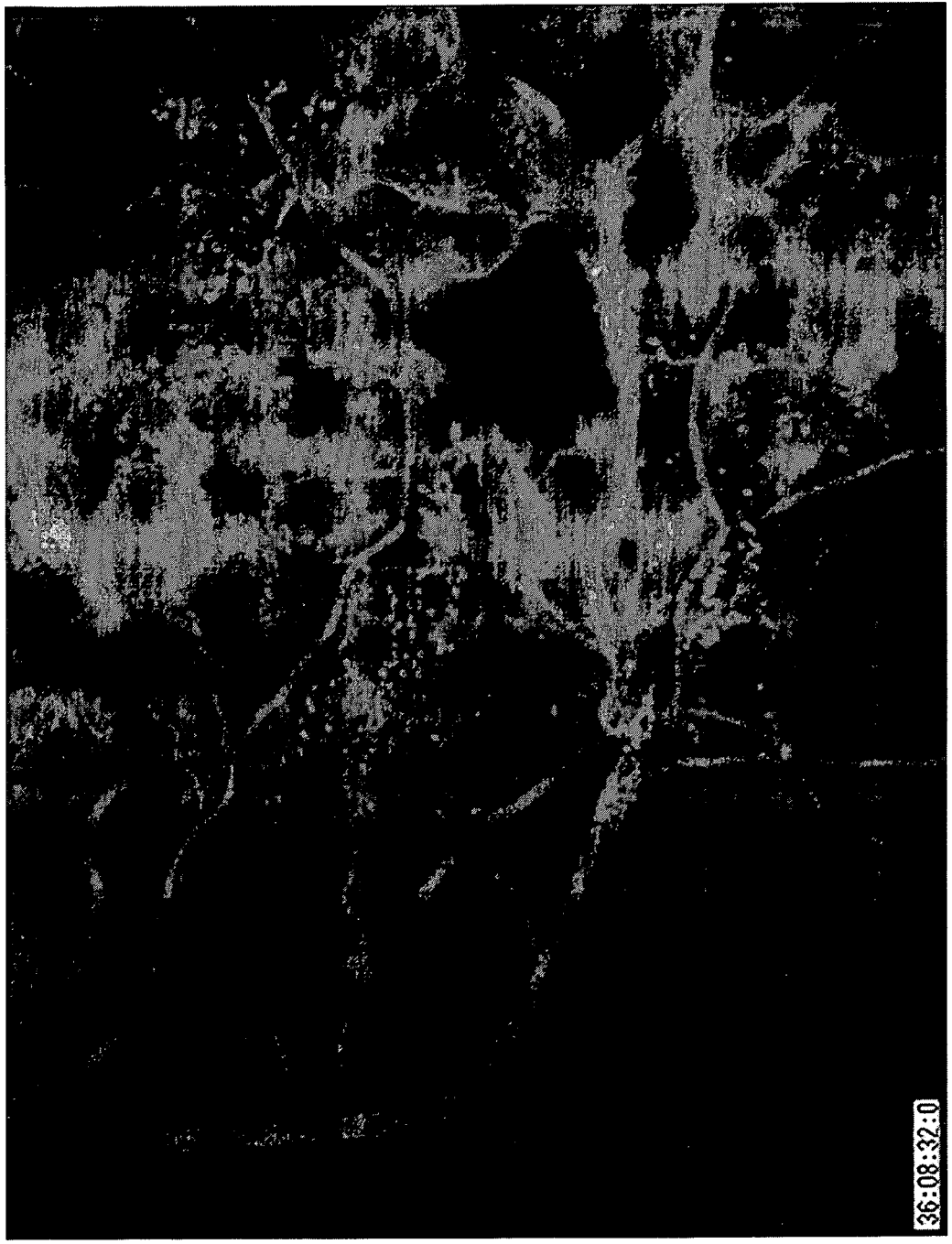
FIG. 7 shows an example of an ordinary fundus image obtained by FAG.
Figure 8:
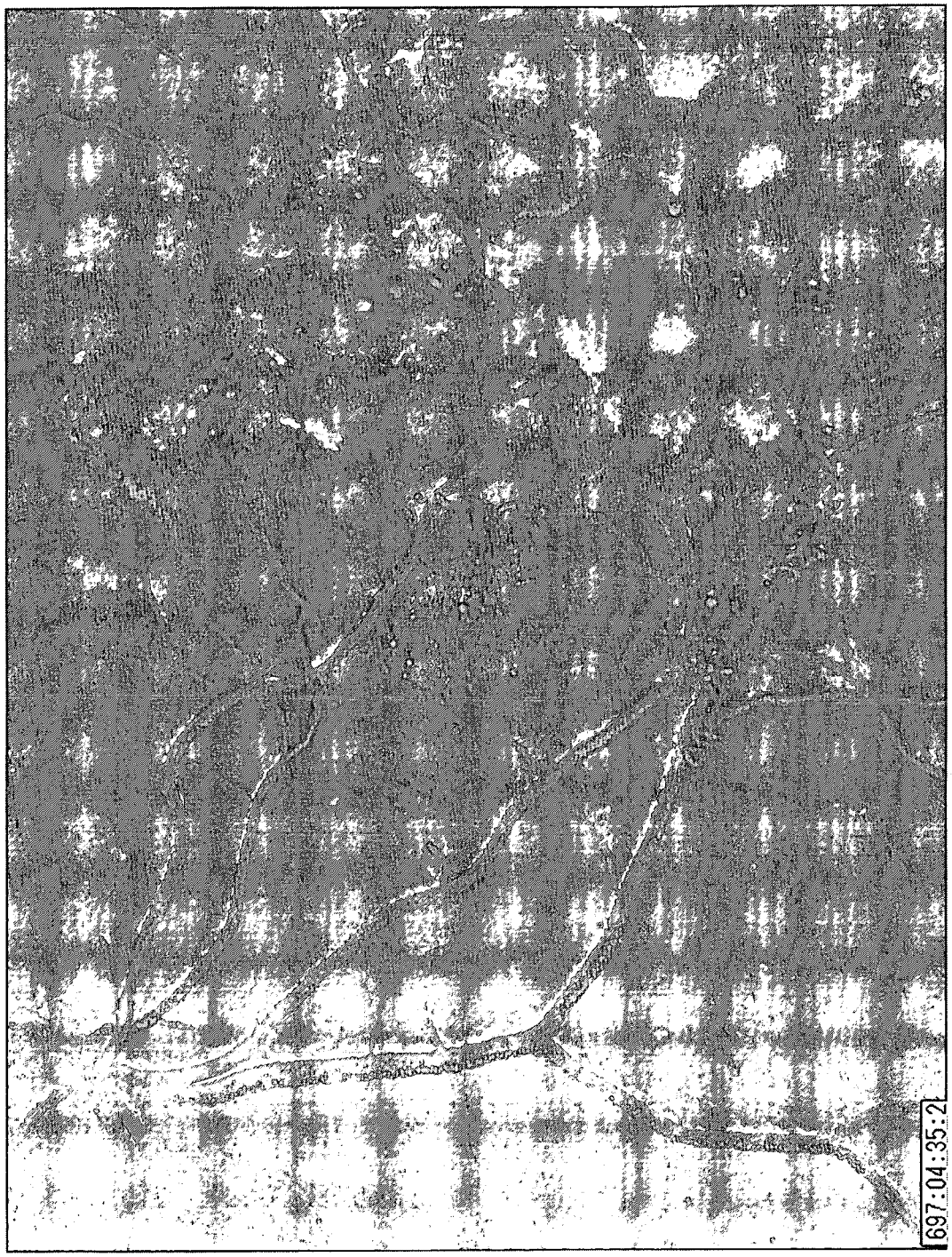
FIG. 8 shows an example of a differential fundus image obtained by FAG.

FIG. 7 shows an example of an ordinary fundus image obtained by FAG and FIG. 8 shows an example of a differential fundus image obtained by FAG immediately after the ordinary fundus image of FIG. 7 is photographed. The right side region of the fundus of FIG. 7 has a portion in which a fluorescent agent has leaked out of the blood vessels and which looks blurred whitely. The whitely blurred portion is not clear, thus making it difficult to identify an affected area. In contrast, in the right side region of the fundus of FIG. 8, minute irregularities in the surface of the fundus are clear. Therefore, the affected area on the fundus is displayed obviously, thereby making it possible to diagnose diabetes etc. effectively.

It is to be noted that in the case of obtaining the differential fundus image, it may be possible to perform the subtractive processing on the output signal from the photoreceptor element 14 after it is quantized; however, the quantization may convert minute changes in the output signal into discrete ones, thus making it difficult to clearly display the minute irregularities in the surface of the fundus and the condition of the affected area.

Figure 9:
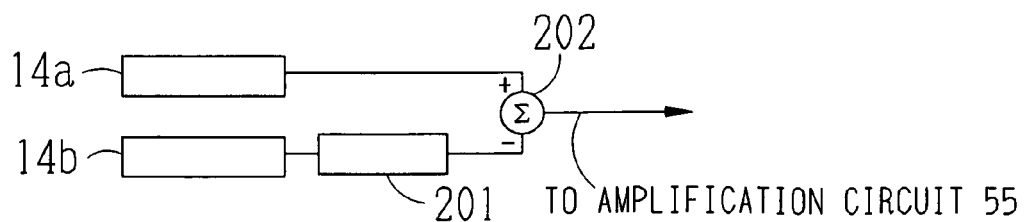
FIG. 9 shows a transformed example of a subtractive processing circuit.

Further, the configuration to obtain time-dependent variations in the output signal from the photoreceptor element 14 is not limited to that described above; for example, two photoreceptor elements 14a and 14b may be used as shown in FIG. 9. In this case, it is necessary only to dispose a light splitting member (for example, half mirror) which splits reflection from the fundus Ef somewhere along the optical path of the photoreceptor optical system so that the photoreceptor elements 14a and 14b may each receive the reflection from the fundus Ef. In this case, a first output signal from the first photoreceptor element 14a is input to the plus side of a subtractor 202 and a second output signal from the second photoreceptor element 14b is delayed time-wise by a delay processing circuit 201 and input to the minus side of the subtractor 202. Thus, the first output signal and the second output signal delayed with respect to the first output signal are subtracted from each other by the subtractor 202, thereby obtaining time-dependent variations in the first output signal.

Although the differential fundus image has been obtained by FAG in the above description, the present invention is not limited to it; for example, it may be obtained by ICG or ordinary fundus photography. It is to be noted that ICG tends to blur the whole image whitely more than FAG, thus finding itself effective in obtaining the differential fundus image.

Further, although the ordinary fundus image display mode and the differential fundus image display mode have been switched from each other through switchover operations in the above description, the present invention is not limited to it; for example, they may be switched automatically (selectively) from each other by the controller 30.

Further, although the fundus image has been obtained in the above description, the present invention is not limited to it; for example, an image of the anterior eye segment etc. may be obtained instead. That is, the present invention can be applied to any method as far as it irradiates the eye of an examinee with light such as a laser beam and receives reflection from the examinee's eye to obtain its image.

What is claimed is:

1. A scanning laser ophthalmoscope comprising:
   a laser source that emits a laser beam;
   an irradiation optical system that scans the laser beam over a fundus two-dimensionally;
   a photoreceptor optical system that receives reflection from the fundus by using a photoreceptor element;
   an image processor that obtains an image of the fundus based on an output signal from the photoreceptor element;
   a monitor; and
   a controller that causes the monitor to display the obtained fundus image,
   wherein the image processor comprises a subtractive processing circuit that performs time-subtractive processing on the output signal from the photoreceptor element in a state where the output signal is input as an analog signal, and forms the fundus image based on the signal subjected to the subtractive processing.

2. The scanning laser ophthalmoscope according to claim 1, wherein the subtractive processing circuit comprises a delay processing circuit that converts the analog-state output signal from the photoreceptor element into a digital signal and performs delay processing on it, and performs addition processing or subtraction processing on the signal subjected to the delay processing and the signal not subjected to the delay processing by respectively using an adder or a subtractor for the time-subtractive processing.

3. The scanning laser ophthalmoscope according to claim 2, wherein the image processor synchronizes a pixel frequency employed when obtaining the signal subjected to the subtractive processing which is worthy of one pixel of the fundus image based on the signal subjected to the subtractive processing with a clock signal frequency employed when converting the analog-state output signal from the photoreceptor element into the digital signal by using the subtractive processing circuit.

4. The scanning laser ophthalmoscope according to claim 1, wherein the image processor selectively forms the fundus image based on the signal subjected to the subtractive processing and the fundus image based on the signal not subjected to the subjective processing.

5. The scanning laser ophthalmoscope according to claim 4, wherein:
   the photoreceptor optical system comprises a filter that transmits a fluorescence generated at the fundus when it is irradiated with the laser beam and that can be inserted into and removed from an optical path of the photoreceptor optical system; and
   the image processor forms the fundus image based on the signal subjected to the subtractive processing if the filter is inserted into the optical path and forms the fundus image based on the signal not subjected to the subtractive processing if the filter is removed from the optical path.

* * * * *